(12) United States Patent
Jasper et al.

(10) Patent No.: US 10,240,088 B2
(45) Date of Patent: Mar. 26, 2019

(54) SUBSTITUTED POLYPHENYLS

(71) Applicant: MERCK PATENT GMBH, Darmstadt (DE)

(72) Inventors: Christian Jasper, Seligenstadt (DE); Timo Uebel, Darmstadt (DE); Detlef Pauluth, Ober-Ramstadt (DE); Michael Junge, Pfungstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 15/519,736

(22) PCT Filed: Sep. 17, 2015

(86) PCT No.: PCT/EP2015/001858
§ 371 (c)(1),
(2) Date: Apr. 17, 2017

(87) PCT Pub. No.: WO2016/058664
PCT Pub. Date: Apr. 21, 2016

(65) Prior Publication Data
US 2017/0240812 A1    Aug. 24, 2017

(30) Foreign Application Priority Data
Oct. 16, 2014  (DE) .................. 10 2014 015 267

(51) Int. Cl.
| | | |
|---|---|---|
| *G02F 1/1333* | (2006.01) | |
| *C09K 19/54* | (2006.01) | |
| *C09K 19/12* | (2006.01) | |
| *C09K 19/30* | (2006.01) | |
| *C07C 25/18* | (2006.01) | |
| *C09K 19/04* | (2006.01) | |

(52) U.S. Cl.
CPC .............. *C09K 19/54* (2013.01); *C07C 25/18* (2013.01); *C09K 19/12* (2013.01); *C09K 19/3001* (2013.01); *C09K 19/3003* (2013.01); *C09K 2019/0448* (2013.01); *C09K 2019/0466* (2013.01); *C09K 2019/125* (2013.01)

(58) Field of Classification Search
CPC .... C09K 19/54; C09K 19/12; C09K 19/3003; C09K 19/3001; C09K 2019/0448; C09K 2019/125; C09K 2019/0466; G02F 1/1333; C07C 25/18
USPC .................................................... 252/299.61
See application file for complete search history.

(56) References Cited

U.S. PATENT DOCUMENTS

| | | | |
|---|---|---|---|
| 7,425,355 B2 | 9/2008 | Klasen-Memmer et al. | |
| 7,754,103 B2 | 7/2010 | Manabe et al. | |
| 8,197,709 B2* | 6/2012 | Lietzau ................. | C09K 19/20 252/299.6 |
| 8,350,100 B2 | 1/2013 | Pauluth et al. | |
| 8,883,037 B2 | 11/2014 | Haase et al. | |
| 9,605,204 B2* | 3/2017 | Manabe ................. | C09K 19/18 |
| 2006/0263544 A1 | 11/2006 | Klasen-Memmer et al. | |
| 2009/0194738 A1 | 8/2009 | Manabe et al. | |
| 2011/0233463 A1 | 9/2011 | Haase et al. | |
| 2012/0149943 A1 | 6/2012 | Pauluth et al. | |
| 2013/0228720 A1 | 9/2013 | Haase et al. | |
| 2014/0284523 A1 | 9/2014 | Furusato et al. | |

FOREIGN PATENT DOCUMENTS

| | | |
|---|---|---|
| EP | 1346995 A1 | 9/2003 |
| EP | 1724324 A1 | 11/2006 |
| WO | 2005123880 A1 | 12/2005 |
| WO | 2010031431 A8 | 5/2011 |

OTHER PUBLICATIONS

International Search Report for PCT/EP2015/001858 dated Dec. 3, 2015.
Lapanik, V. et al., "Thin ferroelectric liquid crystal layers: mechanical stability and fast electro-optical response, connection between molecule design and surface properties," Liquid Crystals, 2013, vol. 40, No. 10, pp. 1391-1397.

* cited by examiner

*Primary Examiner* — Geraldina Visconti
(74) *Attorney, Agent, or Firm* — Millen White Zelano and Branigan, PC

(57) ABSTRACT

The invention relates to substituted quinquephenyls of the formulae indicated in the claims and description. They are particularly suitable as UV-stabilizing component in liquid-crystalline media.

12 Claims, No Drawings

SUBSTITUTED POLYPHENYLS

The invention relates to substituted quinquephenyls for use as components in liquid-crystal mixtures, to liquid-crystal mixtures which comprise the compounds, and to liquid-crystal displays based on these mixtures.

For the purposes of the present application, the term quinquephenyl denotes a structural unit comprising five 1,4-linked benzene rings, where the rings may each additionally be substituted.

Liquid crystals have found widespread use since the first commercially usable liquid-crystalline compounds were found about 30 years ago. Known areas of application of conventional mixtures are, in particular, displays for watches and pocket calculators, and display panels as used in railway stations, airports and sports arenas. Further areas of application are displays of portable and desktop computers, navigation systems and video applications. For the last-mentioned applications in particular, high demands are made of the response times and contrast of the images.

The spatial arrangement of the molecules in a liquid crystal has the effect that many of its properties are direction-dependent. Of particular importance for use in liquid-crystal displays are the optical, dielectric and elastomechanical anisotropies. Depending on whether the molecules are oriented with their longitudinal axes perpendicular or parallel to the two plates of a capacitor, the latter has a different capacitance; in other words, the dielectric constant ε of the liquid-crystalline medium has different values for the two orientations. Substances whose dielectric constant is larger when the longitudinal axes of the molecules are oriented perpendicular to the capacitor plates than when they are oriented parallel are referred to as dielectrically positive. In other words, if the dielectric constant $\varepsilon_\parallel$ parallel to the longitudinal axes of the molecules is larger than the dielectric constant $\varepsilon_\perp$ perpendicular to the longitudinal axes of the molecules, the dielectric anisotropy $\Delta\varepsilon=\varepsilon_\parallel-\varepsilon_\perp$ is greater than zero. Most liquid crystals used in conventional displays fall into this group.

Both the polarisability of the molecule and the permanent dipole moment play a role for the dielectric anisotropy. On application of a voltage to the display, the longitudinal axis of the molecules orients itself in such a way that the larger of the dielectric constants becomes effective. The strength of the interaction with the electric field depends on the difference between the two constants. In the case of small differences, higher switching voltages are necessary than in the case of large differences. The introduction of suitable polar groups, such as, for example, nitrile groups or fluorine, into the liquid-crystal molecules enables a broad range of working voltages to be achieved.

In the case of the liquid-crystalline molecules used in conventional liquid-crystal displays, the dipole moment oriented along the longitudinal axis of the molecules is larger than the dipole moment oriented perpendicular to the longitudinal axis of the molecules. In the most widespread TN ("twisted nematic") cells, a liquid-crystalline layer with a thickness of only from about 5 to 10 µm is arranged between two plane-parallel glass plates, onto each of which an electrically conductive, transparent layer of indium tin oxide (ITO) has been vapour-deposited as electrode. A likewise transparent alignment layer, usually consisting of a plastic (for example polyimides), is located between these films and the liquid-crystalline layer. This alignment layer serves to bring the longitudinal axes of the adjacent liquid-crystalline molecules into a preferential direction through surface forces in such a way that, in the voltage-free state, they lie uniformly with the same orientation, flat or with the same small tilt angle, on the inside of the display surface. Two polarisation films which only enable linear-polarised light to enter and escape are applied to the outside of the display in a certain arrangement.

By means of liquid crystals in which the larger dipole moment is oriented parallel to the longitudinal axis of the molecule, very high-performance displays have already been developed. In most cases here, mixtures of from 5 to 20 components are used in order to achieve a sufficiently broad temperature range of the mesophase and short response times and low threshold voltages. However, difficulties are still caused by the strong viewing-angle dependence in liquid-crystal displays as are used, for example, for laptops. The best imaging quality can be achieved if the surface of the display is perpendicular to the viewing direction of the observer. If the display is tilted relative to the observation direction, the imaging quality deteriorates drastically under certain circumstances. For greater comfort, attempts are being made to maximise the angle through which the display can be tilted from the viewing direction of an observer without significantly reducing the imaging quality. Attempts have recently been made to improve the viewing-angle dependence using liquid-crystalline compounds whose dipole moment perpendicular to the longitudinal axis of the molecule is larger than that parallel to the longitudinal axis of the molecule. The dielectric anisotropy $\Delta\varepsilon$ is negative in this case. In the field-free state, these molecules are oriented with their longitudinal axis perpendicular to the glass surface of the display. Application of an electric field causes them to orient themselves more or less parallel to the glass surfaces. In this way, it has been possible to achieve an improvement in the viewing-angle dependence. Displays of this type are known as VA-TFT ("vertically aligned") displays.

For switching individual pixels, the majority of high-resolution displays are addressed by non-linear electronic elements, for example by thin-film transistors ("TFTs"). Such displays are also referred to below as active-matrix displays (TFT displays).

Besides problems regarding the angle dependence of the contrast and the response times, difficulties also arise in TFT displays due to insufficiently high specific resistance of the liquid-crystal mixtures [TOGASHI, S., SEKOGUCHI, K., TANABE, H., YAMAMOTO, E., SORIMACHI, K., TAJIMA, E., WATANABE, H., SHIMIZU, H., Proc. Eurodisplay 84, Septembe 1984: A 210-288 Matrix LCD Controlled by Double Stage Diode Rings, p. 141 ff, Paris; STROMER, M., Proc. Eurodisplay 84, September 1984: Design of Thin Film Transistors for Matrix Addressing of Television Liquid Crystal Displays, p. 145 ff, Paris]. With decreasing resistance, the contrast of a TFT display deteriorates, and the problem of 'after-image elimination' may occur. Since the specific resistance of the liquid-crystal mixture generally drops over the life of a TFT display owing to interaction with the interior surfaces of the display, a high (initial) resistance is very important in order to obtain acceptable service lives. In particular in the case of low-volt mixtures, it was hitherto impossible to achieve very high specific resistance values. It is furthermore important that the specific resistance exhibits the smallest possible increase with increasing temperature and the lowest possible sensitivity on heating and/or UV exposure. The low-temperature properties of the mixtures from the prior art are also particularly disadvantageous. It is demanded that no crystallisation and/or smectic phases occur, even at low temperatures, and the temperature dependence of the viscosity is as low as possible. The TFT displays from the prior art do not meet today's requirements.

There thus continues to be a great demand for TFT displays having very high specific resistance at the same time as a large working-temperature range, short response times even at low temperatures and low threshold voltage which do not have these disadvantages, or only do so to a reduced extent.

Numerous liquid-crystal mixtures used in TFT displays comprise compounds having limited photostability. Although these compounds are generally stable to natural light—even over an extended period—and can usually also be exposed to UV irradiation for some time without this resulting in decomposition of individual mixture constituents, exposure of the mixtures to, in particular, intense UV radiation for an extended period can result, however, in undesired photochemical processes which partially decompose the compounds of limited photostability and can thus modify the liquid-crystal mixtures in their composition and in their properties in a sensitive manner or even render them unusable. This problem has intensified recently through the fact that the so-called "one-drop filling method" [H. Kamiya, K. Tajima, K. Toriumi, K. Terada, H. Inoue, T. Yokoue, N. Shimizu, T. Kobayashi, S. Odahara, G. Hougham, C. Cai, J. H. Glownia, R. J. von Gutfeld, R. John, S.-C. Alan Lien, *SID* 01 *Digest* (2001), 1354-1357], during the use of which the display cells filled with a liquid-crystal mixture are irradiated with UV light for an extended period in order to effect polymerisation of the monomers used as sealing agent (for example acrylates or epoxides) in order to seal the cells, is now being employed in the manufacture of liquid-crystal displays.

Development in the area of liquid-crystalline materials is still far from complete. In order to improve the properties of liquid-crystalline display elements, attempts are constantly being made to develop novel compounds which enable optimisation of such displays.

Liquid-crystalline mixtures having improved UV stability have already been described in the publication EP 1756248 A. The compounds have four directly connected benzene rings.

It is therefore an object of the present invention to provide compounds having advantageous properties for use in liquid-crystalline media. This is achieved by the use of the compounds of the formula I according to the invention:

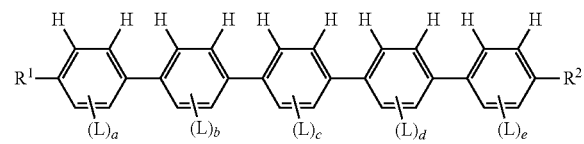

in which
L independently denotes $F_k$, Cl, —CN, an alkyl group having 1 to 5 C atoms, an alkoxy group having 1-5 C atoms or an alkenyl group having 1 to 5 C atoms, preferably F, Cl, methyl or ethyl,
a, b, c, d, e, independently of one another, denote 0, 1 or 2, where a+b+c+d+e>0,
$R^1$ and $R^2$, independently of one another, denote
a) an alkyl group having 1 to 15 C atoms, which may optionally be monosubstituted by CN or at least mono-substituted by halogen, where in each case one or more $CH_2$ groups, in each case independently of one another, may also be replaced by —CH=CH—, —CF=CF—, —CF=CH—, —CH=CF— or —C≡C—,
b) F, Cl, —CN, —NCS, —SF$_5$, —CF$_3$, —CHF$_2$, —CH$_2$F, —OCF$_3$, —OCHF$_2$, —OCH$_2$F,
c) a radical of the formula

in which $R^0$ is defined like $R^1$ under a), or
d) a polymerisable group.

The invention furthermore relates to the use of the compounds of the formula I as component, preferably for the stabilisation, of a liquid-crystalline medium, in particular for a nematic medium.

Preference is given to compounds of the formula I in which $R^1$ and $R^2$ denote a straight-chain, unbranched alkyl group having 1 to 8 C atoms, which may optionally be mono- or polysubstituted by halogen, where in each case one or more $CH_2$ groups, in each case independently of one another, may also be replaced by —CH=CH—, —CF=CF—, —CF=CH—, —CH=CF— or —C≡C—, or a group from definition b), c) or d). Within the meanings of the groups $R^1$ and $R^2$ in accordance with b), the radicals F, Cl, —CN, —NCS, —CF$_3$, —OCF$_3$ and in particular F, —CF$_3$ or —OCF$_3$ are preferred. Preferably, only one of the radicals $R^1/R^2$ has a meaning selected from definition b).

Preference is given to compounds which contain a biphenyl moiety of the formula A, in which the two substituents face away from one another at different ends of the molecule:

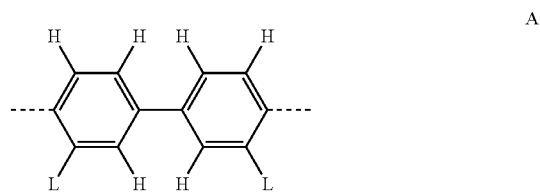

Preference is accordingly given to the following structures:

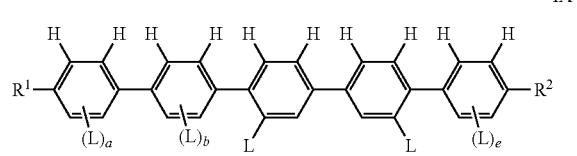

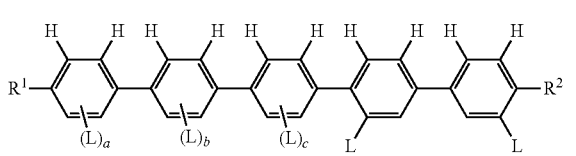

in which the substituents are as defined above and below.

Compounds of the formula I containing branched or substituted wing groups $R^1$ or $R^2$ may occasionally be of importance owing to better solubility in conventional liquid-crystalline base materials. The groups $R^1$ and $R^2$ are preferably not branched and not chiral.

$R^1/R^2$ may represent a polymerisable group inside or outside the general definition of the groups. The groups $R^1/R^2$ therefore additionally denote a polymerisable group, in particular of the formula —(S)$_r$—P, in which S denotes a so-called spacer, i.e., in particular, a 1-15-C alkylene, in which one or more —CH$_2$— may be replaced by —O—, —CO—, —O(CO)— or —(CO)O— in such a way that two oxygen atoms are not adjacent, r denotes 0 or 1, and P denotes a polymerisable group, preferably acryloyl, methacryloyl, oxetanyl, epoxide, vinyl, vinyloxy, propenyloxy or styroyl, in particular acryl or methacryl.

Compounds of the formula I which contain wing groups $R^1$ and/or $R^2$ which are suitable for polymerisation reactions are suitable for the preparation of polymerisable liquid-crystalline mixtures and of resultant liquid-crystalline polymers.

The group $R^1$ preferably denotes an alkyl radical having 1 to 7 C atoms, in particular an alkyl radical having 2 to 6 C atoms. The group $R^2$ preferably denotes an alkyl radical having 1 to 7 C atoms, F, —CN or Cl, in particular an alkyl radical having 2 to 6 C atoms or F.

The number of substituents L in formula I arises from the sum a+b+c+d+e, which can be 1, 2, 3, 4, 5, 6, 7, 8, 9 or 10, preferably 2, 3, 4 or 5 and particularly preferably 2, 3 or 4.

The compounds of the formula I, per se or in mixtures, form liquid-crystalline mesophases in a temperature range which is favourably located for electro-optical use.

The compounds according to the invention are, for the class of polyphenylenes, surprisingly soluble in the usual liquid-crystalline media for display devices. At the same time, compounds having a relatively low melting point have been found. They nevertheless have a high clearing point, or they increase the clearing point of conventional liquid-crystal mixtures. The compounds according to the invention therefore enable broad nematic phase ranges to be achieved.

Besides the excellent properties as liquid-crystalline component, the compounds according to the invention are distinguished, as a special feature, by their action as stabiliser for liquid-crystalline mixtures. The stabilising properties preferably prevent the harmful consequences of UV exposure, which regularly occurs during assembly of the displays and in daily use. With the aid of a stabiliser of this type, it is also possible to use less UV-stable substances, for example those containing C—C double bonds (alkenyl compounds, stilbenes, etc.), in liquid-crystalline mixtures. This gives rise to greater freedom in mixture development, for example through the use of some particularly low-viscosity alkenyl compounds (cf., for example, DE 10224046 A1, EP 834491 A1).

Halogen in connection with the present invention denotes fluorine, chlorine, bromine or iodine, in particular fluorine or chlorine and very particularly fluorine.

The preferred compounds generally have a high tendency towards the formation of nematic liquid-crystalline phases and a high clearing point, as the pure substance or in a mixture with suitable co-components, if the pure substance does not form such a phase.

Particular preference is given to compounds of the formula I according to the invention selected from the following sub-formulae:

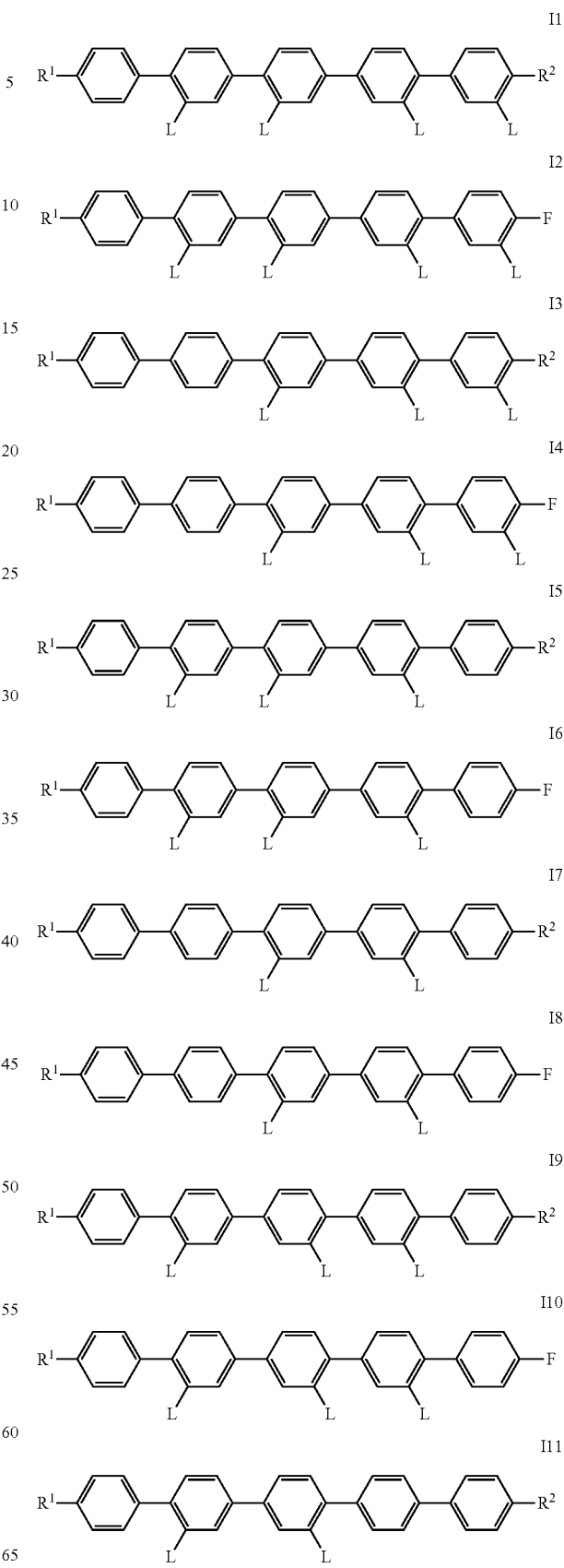

-continued

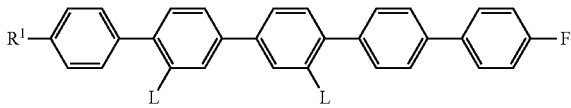
I12

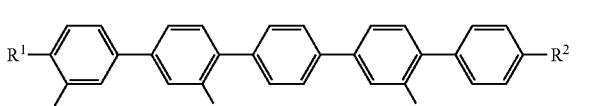
I13

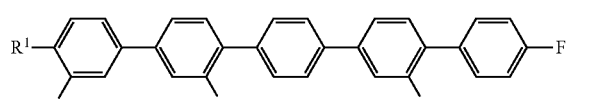
I14

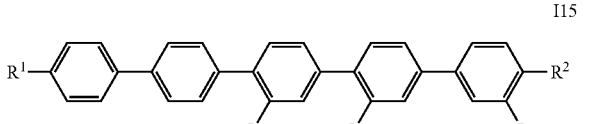
I15

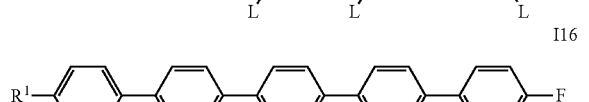
I16 in which the parameters have the respective meanings given above under formula I, and preferably $R^1$ and $R^2$ independently denote an alkyl group having 1 to 15 C atoms, which may optionally be monosubstituted by CN or at least monosubstituted by halogen, where in each case one or more $CH_2$ groups, in each case independently of one another, may also be replaced by —CH=CH—, —CF=CF—, —CF=CH—, —CH=CF— or —C≡C—, and L in each case independently denotes F, Cl, $CH_3$ or $CH_2CH_3$.

Very generally, combinations of the preferred embodiments of the invention indicated above and below and the examples are also to be regarded as particularly preferred, so long as they can formally be combined with one another.

The compounds of the formula I are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail. The compounds of the formula I can advantageously be prepared as can be seen from the following illustrative syntheses (Scheme 1).

A typical preparation process for a number of the compounds according to the invention is one which includes a process step in which a trifluoromethylsulfonylbenzene compound (aryl-OTf) is coupled to an arylboronic acid or an arylboronic acid ester (Scheme 1, third and fifth reaction steps). The trifluoromethylsulfonylbenzene compound is advantageously obtained from the corresponding phenols by esterification using trifluoromethylsulfonic anhydride.

Scheme 1. Illustrative preparation of compounds of the formula I by means of double Suzuki coupling.

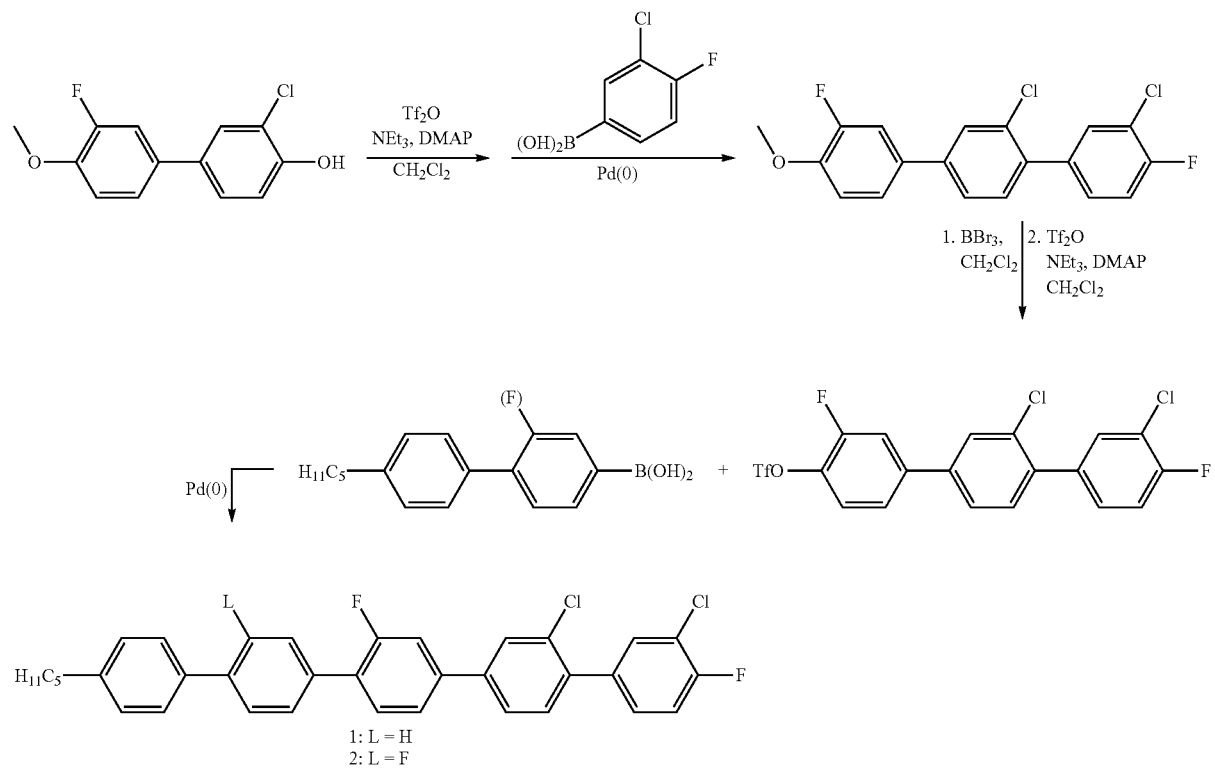

1: L = H
2: L = F

The substituents of the compounds in Scheme 1 can be varied analogously to the general formula I by varying the building blocks employed. In this way, very different compounds according to the invention are achieved. The chemistry proceeds analogously to the synthesis shown by way of example in Scheme 1.

As already mentioned, the compounds of the general formula I can advantageously be used in liquid-crystalline media.

The present invention therefore also relates to a liquid-crystalline medium comprising at least two liquid-crystalline compounds, comprising at least one compound of the formula I.

The present invention also relates to liquid-crystalline media comprising 2 to 40, preferably 4 to 30, components as further constituents besides one or more compounds of the formula I according to the invention. These media particularly preferably comprise 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, 1,3-dioxanes, 2,5-tetrahydropyrans, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid or of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-biscyclohexylbenzenes, 4',4'-biscyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylethanes, 1-phenyl-2-cyclohexylphenylethanes, optionally halogenated stilbenes, benzyl phenyl ethers, tolans and substituted cinnamic acids. The 1,4-phenylene groups in these compounds may also be mono- or polyfluorinated.

The most important compounds suitable as further constituents of media according to the invention can be characterised by the formulae (II), (III), (IV), (V) and (VI):

R'-L-E-R"      (II)

R'-L-(CO)O-E-R"     (III)

R'-L-O(CO)-E-R"     (IV)

R'-L-CH$_2$CH$_2$-E-R"     (V)

R'-L-CF$_2$O-E-R"     (VI)

In the formulae (II), (III), (IV), (V) and (VI), L and E, which may be identical or different, each, independently of one another, denote a divalent radical from the group formed by -Phe-, -Cyc-, -Phe-Phe-, -Phe-Cyc-, -Cyc-Cyc-, -Pyr-, -Dio-, -Thp-, -G-Phe- and -G-Cyc- and their mirror images, where Phe denotes unsubstituted or fluorine-substituted 1,4-phenylene, Cyc denotes trans-1,4-cyclohexylene or 1,4-cyclohexenylene, Pyr denotes pyrimidine-2,5-diyl or pyridine-2,5-diyl, Dio denotes 1,3-dioxane-2,5-diyl, Thp denotes tetrahydropyran-2,5-diyl and G denotes 2-(trans-1,4-cyclohexyl)ethyl, pyrimidine-2,5-diyl, pyridine-2,5-diyl, 1,3-dioxane-2,5-diyl or tetrahydropyran-2,5-diyl.

One of the radicals L and E is preferably Cyc or Phe. E is preferably Cyc, Phe or Phe-Cyc. The media according to the invention preferably comprise one or more components selected from the compounds of the formulae (II), (III), (IV), (V) and (VI) in which L and E are selected from the group Cyc and Phe and simultaneously one or more components selected from the compounds of the formulae (II), (III), (IV), (V) and (VI) in which one of the radicals L and E is selected from the group Cyc and Phe and the other radical is selected from the group -Phe-Phe-, -Phe-Cyc-, -Cyc-Cyc-, -G-Phe- and -G-Cyc-, and optionally one or more components selected from the compounds of the formulae (II), (III), (IV), (V) and (VI) in which the radicals L and E are selected from the group -Phe-Cyc-, -Cyc-Cyc-, -G-Phe- and -G-Cyc-.

In a smaller sub-group of the compounds of the formulae (II), (III), (IV), (V) and (VI), R' and R" each, independently of one another, denote alkyl, alkenyl, alkoxy, alkoxyalkyl (oxaalkyl), alkenyloxy or alkanoyloxy having up to 8 C atoms. This smaller sub-group is called group A below, and the compounds are referred to by the sub-formulae (IIa), (IIIa), (IVa), (Va) and (VIa). In most of these compounds, R' and R" are different from one another, one of these radicals usually being alkyl, alkenyl, alkoxy or alkoxyalkyl (oxaalkyl).

In another smaller sub-group of the compounds of the formulae (II), (III), (IV), (V) and (VI), which is known as group B, E denotes a fluorinated phenylene radical of the formula

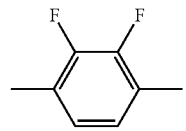

In the compounds of group B, which are referred to by the sub-formulae (IIb), (IIIb), (IVb), (Vb) and (VIb), R' and R" have the meaning indicated for the compounds of the sub-formulae (IIa) to (VIa) and are preferably alkyl, alkenyl, alkoxy or alkoxyalkyl (oxaalkyl).

In a further sub-group of the compounds of the formulae (II), (III), (IV), (V) and (VI), R" denotes —F, —Cl, —CN, —NCS or —(O)$_i$CH$_{3-k}$F$_k$, where i is 0 or 1 and k is 1, 2 or 3. This sub-group is referred to below as group C, and the compounds of this sub-group are correspondingly described by sub-formulae (IIc), (IIIc), (IVc), (Vc) and (VIc). In the compounds of the sub-formulae (IIc), (IIIc), (IVc), (Vc) and (VIc), R' has the meaning indicated for the compounds of the sub-formulae (IIa) to (VIa) and is preferably alkyl, alkenyl, alkoxy or alkoxyalkyl (oxaalkyl).

Besides the preferred compounds of groups A, B and C, other compounds of the formulae (II), (III), (IV), (V) and (VI) having other variants of the proposed substituents are also customary. All these substances are obtainable by methods which are known from the literature or analogously thereto.

Besides the compounds of the general formula I according to the invention, the media according to the invention preferably comprise one or more compounds from groups A, B and/or C. The media preferably comprise one or more compounds from group A and one or more compounds from group B for dielectrically negative mixtures or additionally one or more compounds from group C for dielectrically positive mixtures. The proportions by weight of the compounds from these groups in the media according to the invention are:

Group A:
0 to 90%, preferably 15 to 90%, in particular 20 to 85%.
Group B:
0 to 80%, preferably 10 to 85%, in particular 15 to 80%.
Group C:
0 to 80%, preferably 15 to 90%, in particular 20 to 85%.

The media according to the invention preferably comprise 1 to 40%, particularly preferably 5 to 30%, of the compounds of the formula I according to the invention. Preference is furthermore given to media comprising more than 40%, in particular 45 to 90%, of compounds of the formula I according to the invention. The media preferably comprise one, two, three, four or five compounds of the formula I according to the invention.

The media according to the invention are prepared in a manner conventional per se. In general, the components are dissolved in one another, preferably at elevated temperature. By means of suitable additives, the liquid-crystalline phases of the present invention can be modified in such a way that they can be used in all types of liquid-crystal display element that have been disclosed hitherto. Additives of this type are known to the person skilled in the art and are described in detail in the literature (H. Kelker/R. Hatz, Handbook of Liquid Crystals, Verlag Chemie, Weinheim, 1980). For example, pleochroic dyes can be added for the production of coloured guest-host systems or substances can be added in order to modify the dielectric anisotropy, the viscosity and/or the alignment of the nematic phases.

The invention accordingly relates to a process for the preparation of a liquid-crystalline medium as described above and below, which is characterised in that one or more compounds of the formula I are mixed with one or more further liquid-crystalline compounds and optionally further compounds and additives.

The compounds of the formula I are suitable for use in VA-TFT display systems, for TN-TFT, STN or IPS display systems. Further display types in which compounds according to the invention in liquid-crystal media having correspondingly suitable dielectric properties can be employed are known to the person skilled in the art.

The present invention also relates to electro-optical displays containing a liquid-crystalline medium according to the invention.

In the present application and in the examples below, the structures of the liquid-crystal compounds are indicated by means of acronyms, the transformation into chemical formulae taking place in accordance with Tables A and B below. All radicals $C_nH_{2n+1}$ and $C_mH_{2m+1}$ are straight-chain alkyl radicals having n and m carbon atoms respectively; n, m and k are integers and are preferably 0, 1, 2, 3, 4, 5, 6, 7, 8, 9, 10, 11 or 12. The coding in Table B is self-evident. In Table A, only the acronym for the parent structure is indicated. In individual cases, the acronym for the parent structure is followed, separated by a dash, by a code for the substituents $R^{1*}$, $R^{2*}$, $L^{1*}$ and $L^{2*}$:

| Code for $R^{1*}$, $R^{2*}$, $L^{1*}$, $L^{2*}$, $L^{3*}$ | $R^{1*}$ | $R^{2*}$ |
|---|---|---|
| nm | $C_nH_{2n+1}$ | $C_mH_{2m+1}$ |
| nOm | $C_nH_{2n+1}$ | $OC_mH_{2m+1}$ |
| nO.m | $OC_nH_{2n+1}$ | $C_mH_{2m+1}$ |
| n | $C_nH_{2n+1}$ | CN |
| nN.F | $C_nH_{2n+1}$ | CN |
| nN.F.F | $C_nH_{2n+1}$ | CN |
| nF | $C_nH_{2n+1}$ | F |
| nCl | $C_nH_{2n+1}$ | Cl |
| nOF | $OC_nH_{2n+1}$ | F |
| nF.F | $C_nH_{2n+1}$ | F |
| nF.F.F | $C_nH_{2n+1}$ | F |
| nOCF$_3$ | $C_nH_{2n+1}$ | OCF$_3$ |
| nOCF$_3$.F | $C_nH_{2n+1}$ | OCF$_3$ |
| n-Vm | $C_nH_{2n+1}$ | —CH=CH—$C_mH_{2m+1}$ |
| nV-Vm | $CnH_{2n+1}$—CH=CH— | —CH=CH—$C_mH_{2m+1}$ |

TABLE A

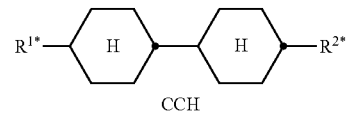

CCH

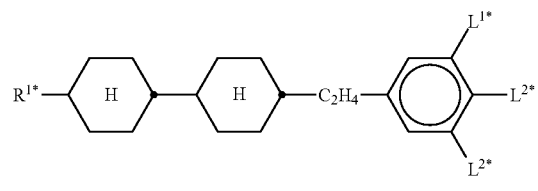

ECCP

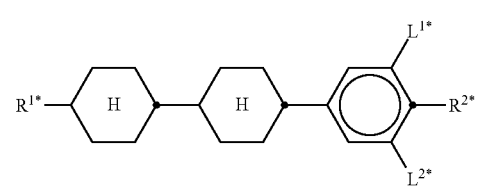

CCP

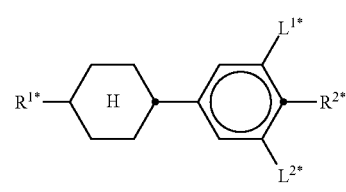

PCH

TABLE B

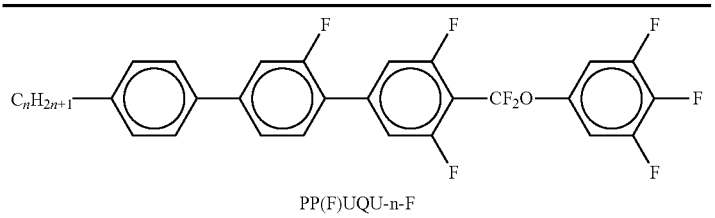

PP(F)UQU-n-F

The following examples are intended to explain the invention without limiting it. Above and below, percentage data denote percent by weight. All temperatures are indicated in degrees Celsius. Furthermore, C=crystalline state, N=nematic phase, Sm=smectic phase and I=isotropic phase. The data between these symbols represent the transition temperatures. Δn denotes the optical anisotropy (589 nm, 20° C.), Δε denotes the dielectric anisotropy (1 kHz, 20° C.) and $\gamma_1$ denotes the rotational viscosity (in the unit mPa·s).

Physical, physicochemical or electro-optical parameters are determined by generally known methods, as described, inter alia, in the brochure "Merck Liquid Crystals—Licristal®—Physical Properties of Liquid Crystals—Description of the Measurement Methods", 1998, Merck KGaA, Darmstadt. Above and below, Δn denotes the optical anisotropy (589 nm, 20° C.) and Δε denotes the dielectric anisotropy (1 kHz, 20° C.). The dielectric anisotropy Δε is determined at 20° C. and 1 kHz. The optical anisotropy Δn is determined at 20° C. and a wavelength of 589.3 nm.

The Δε and Δn values and the rotational viscosity ($\gamma_1$) of the compounds according to the invention are obtained by linear extrapolation from liquid-crystalline mixtures consisting of 5 to 10% of the respective compound according to the invention and 90-95% of the commercially available liquid-crystal mixture ZLI-4792 (for Δε>1, Δn, $\gamma_1$) or ZLI-2857 (for Δε<1) (mixtures, Merck KGaA, Darmstadt).

EXAMPLES

1. Synthesis of 3,2'-dichloro-4,2''-difluoro-4''''-pentyl-[1,1';4',4''; 1'',1''';4''',1'''']-quinquephenyl (4)

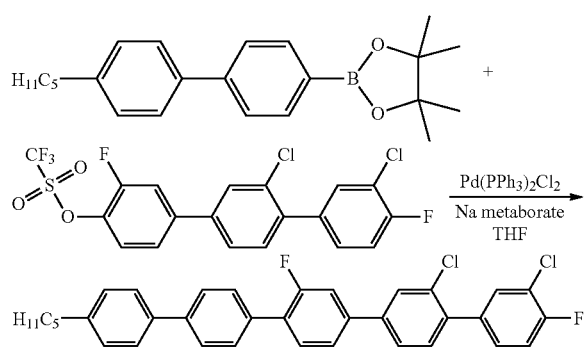

1.1 g (8 mmol) of sodium metaborate are initially introduced in 4 ml of water, and 5 ml of THF, 0.1 g (0.14 mmol) of bis(triphenylphosphine)palladium(II) chloride and a few drops of hydrazinium hydroxide are subsequently added. 1.7 g (4.9 mmol) of the boronic ester and 2.5 g (5.2 mmol) of the triflate compound of the formulae indicated are then added, and the mixture is refluxed for 3 h, 0.5 g (1.4 mmol) of boronic ester are again added, and the mixture is refluxed for a further 12 h.

The batch is cooled, methyl t-butyl ether (MTBE) and water are added, and the phases are separated. The aqueous phase is extracted once with MTBE, the combined organic phases are washed once with water and once with saturated sodium chloride solution, dried over sodium sulfate, filtered and evaporated on a rotary evaporator. The residue is purified by column chromatography (basic aluminium oxide; heptane/toluene) and subsequently recrystallised from ethanol/toluene or heptane, giving the product as a colourless solid.

MS (EI): m/e (%)=556 (100, M⁺), 499 (81, [M-butyl]⁺), 249.5 (35, [M-butyl]²⁺).

C 116 I
Δε=5.8
Δn=0.333
$\gamma_1$=8782 mPa·s

The following are synthesised analogously or comparably:

2. 2''',3''''-Dichloro-2',2'',4''''-trifluoro-4-pentyl-[1,1'; 4',1'';4'',4''';1''',1'''']-quinquephenyl (2)

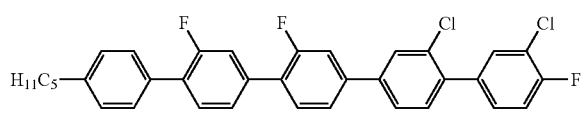

MS (EI): m/e (%)=574 (100, M⁺), 517 (82, [M-butyl]⁺), 258.5 (31, [M-butyl]²⁺).

C 98 SmA 203 N 268.6 I
Δε=3.1
Δn=0.309
$\gamma_1$=10837 mPa·s 3. 4''''-Butyl-2'''-chloro-2',2''-difluoro-4-pentyl-[1,1'; 4',1'';4'',4''';1''',1'''']-quinquephenyl (1)

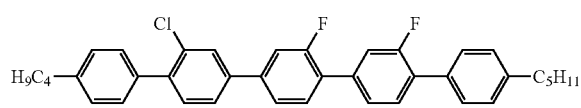

MS (EI): m/e (%)=578 (100, M⁺), 535 (13, [M-propyl]⁺), 521 (40, [M-butyl]⁺), 478 (16, [M-butyl-propyl]⁺), 239 (32, [M-butyl-propyl]²⁺).

C 101 SmA 252 N 330 I
Δε=1.0
Δn=0.330
$\gamma_1$=11203 mPa·s 4. 4-Butyl-2'-chloro-2''-fluoro-4''''-pentyl-[1,1';4',4''; 1'',1''';4''',1'''']-quinquephenyl (3)

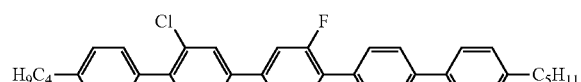

MS (EI): m/e (%)=560 (100, M⁺), 517 (13, [M-propyl]⁺), 503 (50, [M-butyl]⁺), 460 (14, [M-butyl-propyl]⁺), 446 (19), 389 (11), 230 (33, [M-butyl-propyl]²⁺).

Tg −72 C 99 SmC 133 SmA 275 N 351 I
Δε=2.1
Δn=0.345
$\gamma_1$=9534 mPa·s

Further example compounds:

5

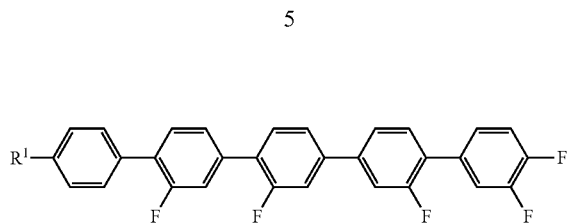

6

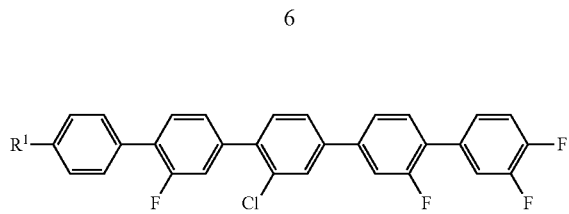

7

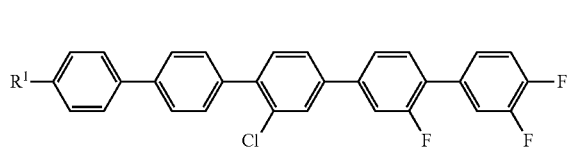

8

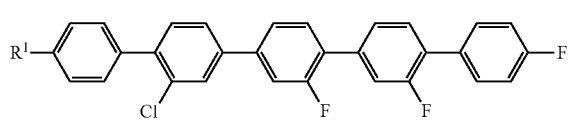

9

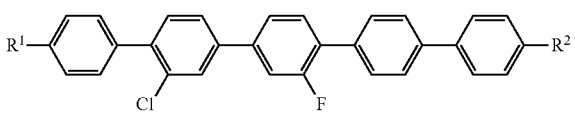

10

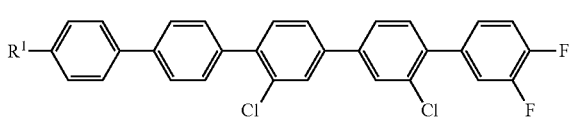

11

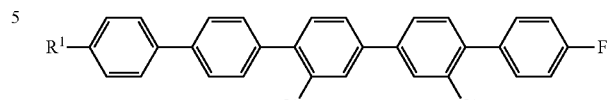

12

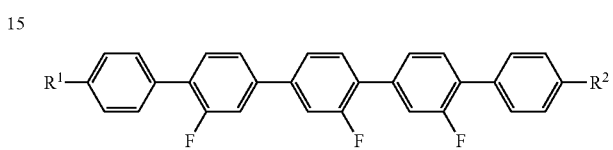

13

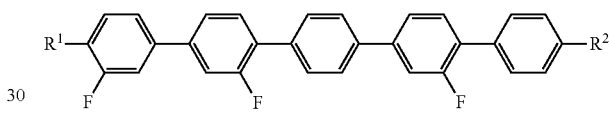

14

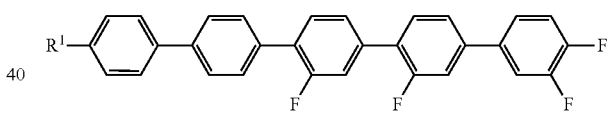

15

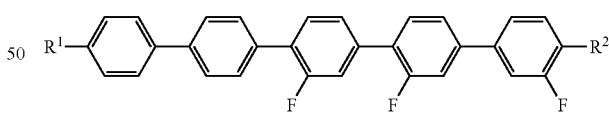

Use Examples: Increasing the Stability of a Liquid-Crystal Mixture to UV Exposure In each case, 0, 0.1 and 1% by weight of the example compounds indicated are added to the following mixture, which is then subjected to a light test for 1 h or 24 h. The light test is carried out using an MTS Atlas Suntest CPS+ instrument. The VHR (voltage holding ratio) measurement value is determined at 100° C.

TABLE 1

Test mixture for the light test.

| Component | Proportion (% by weight) |
|---|---|
| PCH-53 | 18% |
| CCH-35 | 9% |
| CCP-2F.F.F | 10.8% |
| CCP-3F.F.F | 9% |
| CCP-5F.F.F | 7.2% |
| ECCP-3F.F | 9% |
| ECCP-5F.F | 9% |
| CCP-3OCF3.F | 9% |
| CCP-5OCF3.F | 9% |
| PP(F)UQU-3-F | 10% |

The measurement results are shown in Table 2 below.

TABLE 2

VHR measurement values of the test mixture with various additives and variation of the added amount. Measurement after light test (UV exposure) for 1 and 24 h.

| No. | Additive (content) | VHR (24 h) [%] (*) | VHR (1 h) [%] (*) |
|---|---|---|---|
| 1 | None (0% by weight) | 55 | 79 |
| 2 | 1 (0.1% by weight) | 71 | |
| 3 | 1 (1% by weight) | 74 | |
| 4 | 2 (0.1% by weight) | 70 | |
| 5 | 2 (1% by weight) | 75 | |
| 6 | 3 (0.1% by weight) | | 78 |
| 7 | 3 (1% by weight) | | 89 |
| 8 | 4 (0.1% by weight) | | 77 |
| 9 | 4 (1% by weight) | | 88 |

(*) The VHR (voltage holding ratio) value before the light test is about 99%.

The table also shows one reference value each after 1 and 24 h for the mixture without additive. The VHR values are already significantly improved by a small amount of additives, i.e. the mixture is protected against light/UV exposure. The effect is enhanced by increasing the amount of additive.

The invention claimed is:

1. A compound of formula I,

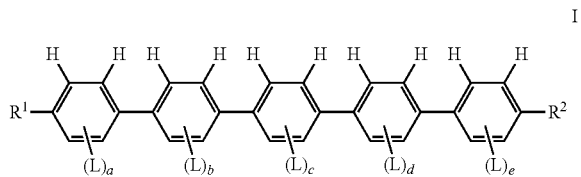

which includes a biphenyl moiety of the formula A

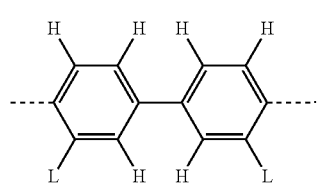

in which

L independently denotes F, Cl, —CN, an alkyl group having 1 to 5 C atoms, an alkoxy group having 1 to 5 C atoms or an alkenyl group having 1 to 5 C atoms, a, b, c, d, e, independently of one another, denote 0, 1 or 2, where a+b+c+d+e>0, $R^1$ and $R^2$, independently of one another, denote
  a) an alkyl group having 1 to 15 C atoms, which may optionally be monosubstituted by CN or at least monosubstituted by halogen, where in each case one or more $CH_2$ groups, in each case independently of one another, may also be replaced by —CH=CH—, —CF=CF—, —CF=CH—, —CH=CF— or —C≡C—,
  b) F, Cl, —CN, —NCS, —$SF_5$, —$CF_3$, —$CHF_2$, —$CH_2F$, —$OCF_3$, —$OCHF_2$, —$OCH_2F$,
  c) a radical of the formula

in which $R^0$ is defined as $R^1$ above,
or
  d) a polymerisable group.

2. A compound according to claim 1, which is selected from the group of the compounds of the formulae IA and IB,

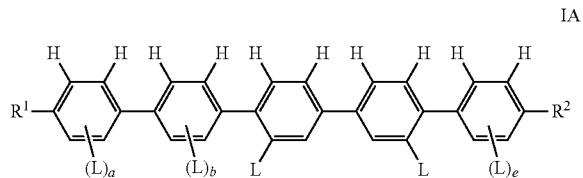

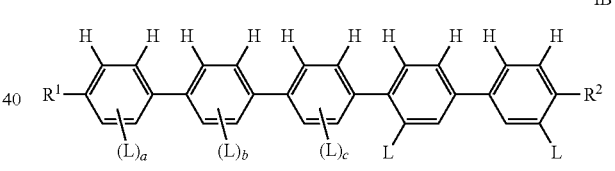

in which $R^1$, $R^2$, L, a, b, c and e independently have the meaning given in claim 1.

3. A compound according to claim 1, selected from the group of the compounds of the formulae

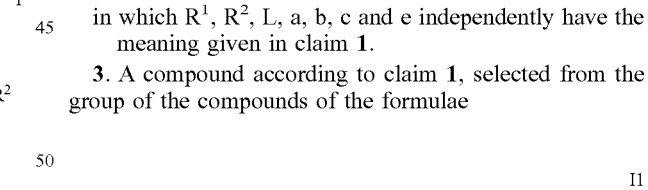

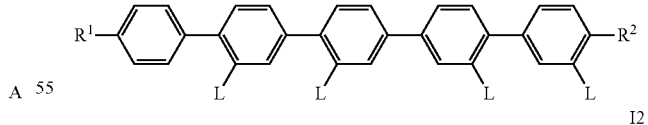

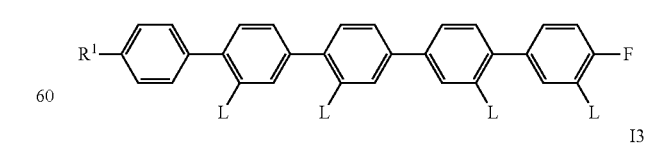

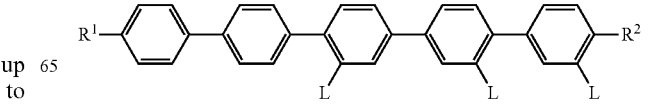

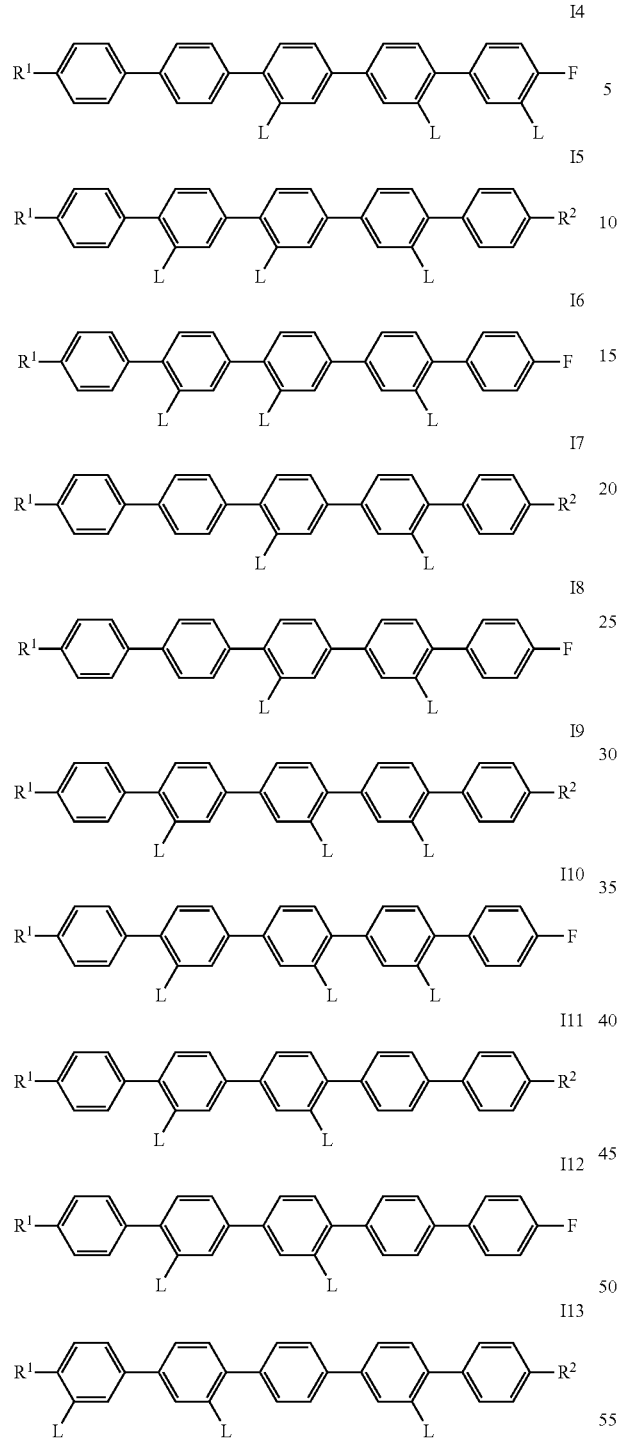

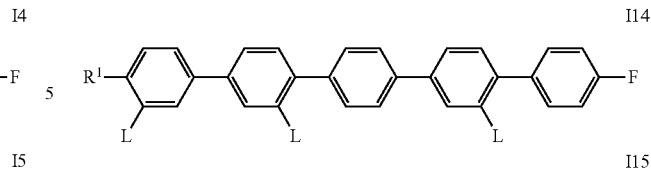

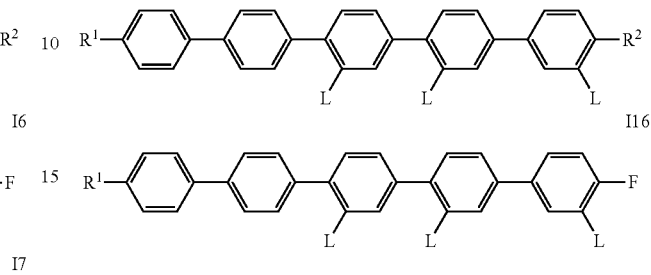

in which the groups $R^1$, $R^2$ and L independently have the meaning given in claim 1.

4. A compound according to claim 1, wherein one, two or three of the substituents L present denote F, Cl or $CH_3$.

5. A compound according to claim 1, wherein
$R^1$ and $R^2$ denote a straight-chain, unbranched alkyl group having 1 to 8 C atoms, which may optionally be mono- or polysubstituted by halogen, where in each case one or more $CH_2$ groups, in each case independently of one another, may be replaced by —CH=CH—, —CF=CF—, —CF=CH—, —CH=CF— or —C≡C—,
or a group from definition b), c) or d) according to claim 1.

6. A compound according to claim 1, wherein one or more of the groups L denotes fluorine.

7. A method which comprises including in a liquid-crystal medium a compound according to claim 1 as a component for the stabilisation of said liquid-crystal medium.

8. A liquid-crystal medium comprising at least two liquid-crystalline compounds, characterised in that it comprises one or more compounds of the formula I according to claim 1.

9. A method which comprises including a liquid-crystal medium according to claim 8 in an electro-optical display.

10. An electro-optical display containing a liquid-crystal medium according to claim 8.

11. A process for the preparation of a liquid-crystalline medium according to claim 8, wherein one or more compounds of the formula I are mixed with one or more further liquid-crystalline compounds, and further compounds and additives are optionally added.

12. A compound according to claim 1, wherein each L independently denotes F or Cl.

\* \* \* \* \*